(12) United States Patent
Osman

(10) Patent No.: US 12,109,361 B1
(45) Date of Patent: *Oct. 8, 2024

(54) SYSTEM AND METHOD FOR VIDEO ASSISTED PERCUTANEOUS NEEDLE CRICOTHYROTOMY AND TRACHEOSTOMY

(71) Applicant: Ali Osman, Beaumont, TX (US)

(72) Inventor: Ali Osman, Beaumont, TX (US)

( * ) Notice: Subject to any disclaimer, the term of this patent is extended or adjusted under 35 U.S.C. 154(b) by 71 days.

This patent is subject to a terminal disclaimer.

(21) Appl. No.: 18/085,488

(22) Filed: Dec. 20, 2022

Related U.S. Application Data

(63) Continuation of application No. 16/662,740, filed on Oct. 24, 2019, now Pat. No. 11,559,646.

(Continued)

(51) Int. Cl.
| | | |
|---|---|---|
| *A61M 16/04* | (2006.01) | |
| *A61B 1/00* | (2006.01) | |
| *A61B 1/05* | (2006.01) | |
| *A61B 1/07* | (2006.01) | |
| *A61B 17/34* | (2006.01) | |

(Continued)

(52) U.S. Cl.
CPC ..... *A61M 16/0488* (2013.01); *A61B 1/00045* (2013.01); *A61B 1/00114* (2013.01); *A61B 1/05* (2013.01); *A61B 1/07* (2013.01); *A61B 17/3417* (2013.01); *A61B 17/3423* (2013.01); *A61M 29/02* (2013.01); *A61B 2017/00557* (2013.01); *A61B 2017/3454* (2013.01); *A61M 2205/3306* (2013.01)

(58) Field of Classification Search
CPC .............. A61M 16/0488; A61M 29/02; A61M 2205/3306; A61B 1/00045; A61B 1/00114; A61B 1/05; A61B 1/07; A61B 17/3417; A61B 17/3423; A61B 2017/00557; A61B 2017/3454

See application file for complete search history.

(56) References Cited

U.S. PATENT DOCUMENTS

| 4,976,261 | A | * | 12/1990 | Gluck | ............... A61M 16/0486 |
|---|---|---|---|---|---|
| | | | | | 128/207.14 |
| 5,205,286 | A | * | 4/1993 | Soukup | ............... A61B 5/0031 |
| | | | | | 600/377 |

(Continued)

*Primary Examiner* — Anh Tuan T Nguyen
*Assistant Examiner* — Shankar Raj Ghimire
(74) *Attorney, Agent, or Firm* — David Colls; Berger Singerman LLP

(57) ABSTRACT

A system and method for video assisted percutaneous needle cricothyrotomy and tracheostomy to assist physicians in quickly intubating patients suffering from respiratory distress when oral or nasal intubation is not possible or contraindicated. The system and method includes a display monitor, a percutaneous needle assembly including a connection hub having a syringe port for removably attaching a syringe, a needle port for attaching a hollow needle, and a stylet port in communication with the needle port for receiving a fiber optic stylet that extends through the hollow needle. The fiber optic stylet includes one or more illuminators, and a camera for capturing and transmitting anatomical images for display on the display monitor to visually assist physicians in locating a patient's trachea lumen. The fiber optic stylet is positioned within the trachea lumen, and used as a guide wire to insert a dilator and cannula for ventilating the patient.

20 Claims, 11 Drawing Sheets

Related U.S. Application Data

(60) Provisional application No. 62/845,412, filed on May 9, 2019, provisional application No. 62/918,732, filed on Feb. 11, 2019.

(51) Int. Cl.
*A61M 29/02* (2006.01)
*A61B 17/00* (2006.01)

(56) References Cited

U.S. PATENT DOCUMENTS

| | | | | |
|---|---|---|---|---|
| 5,217,005 A * | 6/1993 | Weinstein | A61M 16/0472 128/207.14 |
| 5,419,314 A * | 5/1995 | Christopher | A61M 16/0475 128/207.29 |
| 5,431,676 A * | 7/1995 | Dubrul | A61B 17/3439 606/191 |
| 5,573,517 A * | 11/1996 | Bonutti | A61B 17/0401 606/198 |
| 5,653,230 A * | 8/1997 | Ciaglia | A61M 16/0431 128/200.26 |
| 5,797,879 A * | 8/1998 | DeCampli | A61B 5/6876 604/93.01 |
| 5,840,013 A * | 11/1998 | Lee | A61B 1/32 600/114 |
| 5,921,917 A * | 7/1999 | Barthel | A61B 1/07 128/200.26 |
| 6,706,017 B1 * | 3/2004 | Dulguerov | A61M 16/085 128/207.29 |
| 7,036,510 B2 * | 5/2006 | Zgoda | A61M 16/0445 128/207.14 |
| 7,946,981 B1 * | 5/2011 | Cubb | A61B 1/00103 600/187 |
| 8,151,791 B2 * | 4/2012 | Arlow | A61M 16/0472 128/207.14 |
| 8,307,824 B2 * | 11/2012 | Cuevas | A61M 16/0472 128/207.14 |
| 9,610,007 B2 * | 4/2017 | Kienzle | A61B 1/00098 |
| 9,861,800 B2 * | 1/2018 | Alexander | A61B 1/00135 |
| 10,722,322 B2 * | 7/2020 | Vazales | A61M 16/0488 |
| 11,051,851 B2 * | 7/2021 | Einarsson | A61B 1/00096 |
| 11,166,629 B2 * | 11/2021 | Ochi | A61B 1/317 |
| 2007/0255258 A1 * | 11/2007 | Matlock | A61M 16/0427 604/535 |
| 2008/0086074 A1 * | 4/2008 | Taylor | A61B 1/0008 600/114 |
| 2008/0140023 A1 * | 6/2008 | McMillan | A61B 18/20 604/272 |
| 2008/0188812 A1 * | 8/2008 | Valaie | A61M 25/0606 604/164.01 |
| 2008/0234670 A1 * | 9/2008 | Rogers | A61N 5/0624 606/12 |
| 2009/0320854 A1 * | 12/2009 | Cuevas | A61M 16/0472 128/207.29 |
| 2012/0089023 A1 * | 4/2012 | Schlager | A61M 16/0418 600/529 |
| 2012/0149980 A1 * | 6/2012 | Pacey | A61B 1/267 600/109 |
| 2014/0073926 A1 * | 3/2014 | Rajendran | A61M 25/0108 600/478 |
| 2014/0128902 A1 * | 5/2014 | Guerra | A61M 16/0472 606/196 |
| 2015/0250969 A1 * | 9/2015 | Xavier | A61M 16/0816 128/200.26 |
| 2016/0038031 A1 * | 2/2016 | Margallo Balbás | A61B 1/07 600/478 |
| 2016/0174819 A1 * | 6/2016 | Ouyang | A61B 1/00098 600/105 |
| 2016/0296719 A1 * | 10/2016 | Geraghty | A61M 16/085 |
| 2017/0014019 A1 * | 1/2017 | Ogura | A61B 1/00114 |
| 2017/0042573 A1 * | 2/2017 | Savvouras | A61B 1/00154 |
| 2017/0055813 A1 * | 3/2017 | London Brown | A61B 1/00154 |
| 2017/0135561 A1 * | 5/2017 | Snoke | A61B 1/00066 |
| 2017/0173275 A1 * | 6/2017 | Anderson | A61B 5/0084 |
| 2018/0084986 A1 * | 3/2018 | Ochi | A61B 17/3496 |
| 2018/0168768 A1 * | 6/2018 | Mirsepassi | A61F 9/008 |
| 2020/0214739 A1 * | 7/2020 | Shi | A61B 1/05 |
| 2020/0245854 A1 * | 8/2020 | Mach | A61B 1/00167 |
| 2021/0251789 A1 * | 8/2021 | Ouyang | A61B 1/00052 |
| 2021/0330354 A1 * | 10/2021 | Einarsson | A61B 90/361 |

\* cited by examiner

SYSTEM AND METHOD FOR VIDEO ASSISTED PERCUTANEOUS NEEDLE CRICOTHYROTOMY AND TRACHEOSTOMY

CROSS-REFERENCE TO RELATED APPLICATIONS

This application claims the benefit of U.S. Nonprovisional patent application Ser. No. 16/662,740, filed on Oct. 24, 2019, and Provisional patent Application Ser. No. 62/918,732, filed on Feb. 11, 2019, and of U.S. Provisional patent Application Ser. No. 62/845,412, filed on May 9, 2019, all of which are incorporated by reference herein in their entirety.

FIELD OF THE INVENTION

The present invention relates to medical systems and methods, and more particularly, to a system and method for video assisted emergency percutaneous needle cricothyrotomy and tracheostomy for visually locating a patient's trachea when performing surgical airway procedures as life a saving measure to ventilate and oxygenate patients.

BACKGROUND OF THE INVENTION

There are emergent circumstances in which individuals need ventilation or respiratory support because of respiratory failure attributed to inadequate levels of arterial oxygen or elevated levels of carbon dioxide, or both. Various causes that lead to respiratory distress include, for example, hypoxemia, which involves insufficient or low levels of oxygen in the blood that are often associated with certain medical conditions such as anemia, pneumonia, or pulmonary edema, chronic obstructive pulmonary disorder (COPD), asthma, drug overdoses, allergic reactions due to insect bites or foods, or as a result of exposure to various medications or dyes associated with certain medical procedures such as dye-contrast stress tests, or magnetic resonance imaging tests. In emergencies where patients suffer from respiratory failure, it is vital for the patient to be quickly and adequately oxygenated and ventilated as time is of the essence to mitigate damage because of the patient having low oxygen levels. There are circumstances when patients suffering from respiratory failure are timely admitted in a hospital emergency, however, unpredictable situations often lead to moments where there is absolutely no time to transport patients to a hospital, or emergency care center, because the patient must be oxygenated or ventilated quickly to sustain life.

The standard protocols used in oxygenating and ventilating individuals who suffer from respiratory failure typically include non-invasive or invasive oxygen or ventilation therapy. Non-invasive therapy typically involves giving patients prescribed concentrations of oxygen using bag-valve mask ventilation, nasal air prongs, or continuous positive airway pressure machines. Such conventional methods often comprise the first steps to treat patients in need of ventilation support but who do not suffer from profound respiratory failure. If non-invasive steps taken to create a patient airway are unsuccessful, then efforts are directed to invasive ventilation support that is needed to manage a patient's airway and satisfy the imminent need of oxygen because of the heighted concern of respiratory distress Invasive approaches often entail ventilation strategies that involve laryngeal mask, endotracheal, or nasotracheal intubation. Intubation generally involves inserting a flexible plastic tube, having a designated diameter, within a patient's mouth or nose, and positioning the tube within the patient's trachea to maintain an open airway for introducing oxygen, or medical drugs into the patient. The tube provides a conduit to deliver oxygenated air to the person's lungs. Correctly inserting the intubation tube is of critical importance, and often requires the attending physician to determine whether the traditional intubation method will benefit the patient in pulmonary distress, and whether the patient's anatomical condition is conducive for sustaining intubation. For example, the patient may have a difficult anatomy, may be obese, may have limited neck mobility or a thick neck, may have a physical obstruction such as a mass or object that is present in the person's airway, may have facial trauma, may have a hematoma, or may have excessive secretion making it difficult or near impossible for successfully intubate the patient. As such, a patient's restrictive anatomical condition will often require a more invasive surgical procedure to secure an open airway. Performing a surgical airway on a patient is preferably the last resort in managing a patient's respiratory failure when previous attempts to intubate or ventilate the patient using traditional methods such as bag-valve, laryngeal mask ventilation, or endotracheal/nasotracheal intubation, were either not possible, unsuccessful, ineffective, or contraindicated.

At the point of reaching invasive medical intervention, the patient has likely risen to a critical stage where the patient is hypoxic with oxygen saturation levels dropping. It is imperative at this stage that a surgical airway procedure be done quickly and correctly or the patient will suffer severe brain damage, or even death. The surgical airway procedure is by far more intensive, very stressful, and riddled with anxiety as compared to conventional non-invasive respiratory therapies, or intubation. In practice, the surgical airway procedure known as surgical cricothyrotomy involves properly locating and identifying the patient's cricothyroid membrane, which is anatomically located between the thyroid and cricoid cartilage, making the necessary incision through the membrane, and subsequently inserting a hollow tube, such as an air cannula, through the cricothyroid membrane and into the patient's trachea to properly ventilate the patient while being performed at a fast pace, and in a short period of time. Determining the correct anatomical location to place the air cannula in the patient is the most critical aspect of the procedure. In conventional practice, practitioners often rely on anatomical landmarks to assist them in accurately locating and identifying the cricothyroid membrane and tracheal ring in an effort to insert the air cannula in the correct position. The procedure generally requires palpating the region of the patient's neck to properly locate the cricothyroid membrane or notch, sometimes even marking the target puncture site with a marker or pen in order to visually identify the exact area on the patient's neck to make an incision. Relying on anatomical landmarks to locate the cricothyroid membrane is difficult and challenging even to the most experienced physicians. Difficulty in determining the cricothyroid membrane is compounded with patients who are obese, or have short or thick necks. Such anatomical challenges are a primary reason for failed endotracheal intubation in the first place. The procedure is very intense because during the process, the patient is severely struggling for air with every minute that passes, and any failed or delayed surgical airway management can lead to permanent disability, brain damage, or death. Successful placement of an air cannula, during cricothyrotomy or tracheostomy procedures, depends highly on the accurate and rapid identification of anatomical landmarks of the cricothyroid membrane and the patient's trachea.

Various instruments or tools have been developed to better assist physicians in performing surgical airway procedures on patients in hospital emergencies, intensive care units, operating rooms, in ambulances, or directly in the field. One practice involves replacing the traditional use of a scalpel used to make an incision, with a needle to allow physicians to pass a catheter or dilator over the needle to insert the dilator into the patient's trachea to ventilate the patient. Such approach has shown to cause less damage and trauma to patients, and provide a mechanism for introducing an air cannula having a larger diameter through the small incision with ease. Still, use of a needle alone has proven challenging because physicians must often have to re-stick patients as a result of incorrectly locating the correct anatomical region needed to ventilate patients, resulting in loss of time, and greater discomfort and damage caused to patients.

Advanced developments have made improvements to various tools and devices commonly used by doctors when performing such surgical airway procedures. For example, some prior art devices have improved functionality of needles by providing depth penetration indicators to assist physicians in determining how far a needle should be inserted within a patient, other improvements have redesigned needles to mitigate tissue damage when piercing a patient's skin, and some have provided instruments with ergonomic handles designed to better handle and manipulate the tool during use. Unfortunately, such improvements have not abated the difficulty physician's face in properly identifying and locating the correct anatomical regions of a patient when needing to insert an air cannula quickly and efficiently during emergency surgical airway procedures. Unsuccessful attempts at placing a cuffed or regular cannula in the cricoid membrane is often due to the fact that the cannula is simply not positioned correctly in the trachea, the cannula shifts or flips out of position during use, or the tip of the cannula rests on soft tissue around the neck when the physician believes the cannula is in the tracheal lumen. Removing and attempting to reposition the air cannula causes excessive bleeding or tissue damage, punctures blood vessels, causes damage to anatomical structures of the patient's neck, causes loss of precious time, and renders the procedure difficult to re-do a second time around because of tissue damage and bleeding. The time wasted in making repeated attempts at correctly locating the position to insert the air cannula can result in a patient's disability or death. The use of conventional devices that include structural improvements, or provide limited benefits, do not provide the proper and effective guidance needed in locating a patient's trachea for optimally performing emergency cricothyrotomy.

Still, as a result of deficiencies in improvements, more advanced system and devices have been introduced to assist medically trained individuals in performing surgical airway procedures. Visual positioning medical appliances such as tubes or cannulas is often accomplished using ultrasound systems, video laryngoscopes, endoscopes, or endotracheal devices that are electrically coupled to an image-capturing device. However, very little technology is currently available, or has been developed, to better assist physicians in efficiently and correctly locating and identifying anatomical regions, such as a person's trachea when undergoing emergent cricothyrotomy. Although some prior art systems employ image-capturing devices, such devices generally include an imaging probe that is used solely for visual navigation through a patient's nose, throat, ears, or arteries, and provides no other functional benefit but to capture images. Further, many image capturing devices are used with patients where the exact anatomical location for inserting an air cannula has already been identified in a previous surgical setting, thus eliminating the urgent need for correctly identifying and locating anatomical region during emergent circumstances without the benefit of prior identification of anatomical regions. In addition, most image capturing devices on the market are large in size, bulky, awkward to use, and are not adapted for use with over-needle installation of air cannula/dilator procedures.

Accordingly, there is an established need for a solution to at least one of the aforementioned problems. There remains a need for a system and method for video assisted percutaneous needle cricothyrotomy and tracheostomy that allows physicians to view displayed images of a patient's tracheal lumen to quickly intubate and ventilate patients during emergent surgical airway procedures. There also remains a need for a system and method for video assisted percutaneous needle cricothyrotomy that allows physicians to efficiently insert an air cannula, in a patient's trachea, where the patient has restricting, anatomical features while making less damage to the patient's neck, tissue, and blood vessels to effectively ventilate and oxygenate patients.

SUMMARY OF THE INVENTION

The present invention is directed to a system and method for video assisted percutaneous needle cricothyrotomy and tracheostomy for patients in respiratory distress including a display monitor, a percutaneous needle assembly including a syringe, a connection hub including a syringe port for removably attaching the syringe, a needle port for attaching a hollow needle including a beveled tip, and a stylet port for receiving a fiber optic stylet that extends into the hollow needle, and includes one or more illuminators and a camera for capturing and transmitting images of a patient's anatomical features including the tracheal lumen to the display monitor. The fiber optic stylet is used a medical guidewire to insert an air cannula into a patient's cricothyroid membrane, and trachea to ventilate and oxygenate patients.

A first embodiment of the invention provides a system providing video assistance for locating a patient's tracheal lumen when performing surgical airway procedures including percutaneous needle cricothyrotomy and tracheostomy to properly ventilate the patient during respiratory distress, where the system comprises: a display monitor including a viewing screen for displaying still or video images, a percutaneous needle assembly including a connection hub having a syringe port, a needle port, a stylet port in communication with the needle port, a hollow needle releasably attached to the needle port and including a beveled tip, and a syringe including a cavity for holding a liquid or gas, and a syringe tip in fluid communication with the cavity, and a plunger associated with the cavity and operated to extract or retract a liquid or gas through the syringe tip, where the syringe tip is removably attached to the syringe port, a fiber optic stylet having a distal end including an image capturing device, and at least one illuminator, and a proximate end, where the distal end is removably insertable through the stylet port to extend through the needle port and slide within the hollow needle when the needle is affixed to the needle port, a communication module, where the proximate end of the fiber optic stylet is operatively coupled to the communication module, a communication cable having a one end operatively coupled to the display monitor, and a second end operatively coupled to the communication module, where the image capturing device, and at least one illuminator are operatively controlled by the display monitor via, the communication module; and wherein the beveled tip of the hollow needle, and the distal end of the fiber optic stylet are removably inserted within an anatomical region of the patient where the image capturing device is operated to capture images, and transmit signals associated with the captured images to the display monitor where the display monitor receives and processes said transmitted signals to display the captured images on the viewing screen, and the at least one illuminator is operated to illuminate a frontal region of the image capturing device.

In one aspect, the connection hub includes a release lock provided on the stylet port for releasably engaging the fiber optic stylet when the fiber optic stylet is disposed within the stylet port to prevent the fiber optic stylet from sliding freely within the hollow needle.

In one aspect, the image-capturing device comprises a camera. The camera may include a charge-coupled device (CCD), or a complementary metal oxide semiconductor (CMOS) image sensor.

In another aspect, the at least one illuminator includes a plurality of illuminators each comprising a light emitting diode, or one or more fiber optic stylets coupled to an illuminating source, each of the plurality of illuminators surrounding the camera.

In one aspect, the distal end of the fiber optic stylet comprises a beveled end including the plurality of illuminators and the camera.

In one aspect, the release lock selectively engages the fiber optic stylet when the beveled end of the fiber optic stylet is coplanar with the beveled tip of the hollow needle to allow inserting both the beveled end and the beveled tip simultaneously within an anatomical region comprising a patient's cricothyroid membrane. The release lock selectively disengages the fiber optic stylet to permit a portion of the fiber optic stylet to advance forward and extend within the tracheal lumen when the beveled end of the fiber optic stylet enters the tracheal lumen, where a portion of the fiber optic stylet bends at an angle away from the beveled tip of the hollow needle when the portion is displaced within the tracheal lumen.

In one aspect, the captured images comprise images of a patient's tracheal lumen that is displayed on the viewing screen of the display monitor.

In another aspect, the system further includes a dilator having a dilator tube including an elongate aperture extending through the body of the dilator tube for receiving and sliding over the fiber optic stylet, and a cannula including a cannula tube having an opening for receiving the dilator therein. The cannula tube includes an inflatable air cuff, and an air delivery connector in fluid communication with the inflatable air cuff, where the air delivery connector is attachable to an air supply for delivering air to the inflatable air cuff. The cannula tube includes a hub and a cannula stopper that extends outwards from opposite sides of the hub and perpendicular to the cannula tube. The dilator tube and cannula tube slide over the fiber optic stylet and are both simultaneously inserted within the patient's cricothyroid membrane and tracheal lumen.

In one aspect, the dilator tube is removed from the cannula tube after the cannula tube is fully inserted within the patient's tracheal lumen, where the inflatable air cuff is inflated to secure the cannula tube in place within the patient's trachea lumen.

In another aspect, the connection hub includes a surrounding wall having a top and a bottom, where the syringe port extends upwards from the top, the needle port extends downwards from the bottom, and the stylet port extends outwards at an angle from the connection hub.

In one aspect, the display monitor comprises a portable display monitor, and/or a color display monitor.

In another aspect, a method of performing a cricothyroidotomy or a tracheostomy with a video-assisted system on a person is provided. The method generally includes the steps of providing a video-assisted system as generally described herein, locating an insertion site, such as a tracheal or cricothyroid ring, inserting the needle into a desired anatomical region with the tip of the needle facing toward the patient's feet, advancing the fiber optic stylet further into the anatomical region, removing the needle from the first anatomical region leaving the fiber optic stylet in the second anatomical region, advancing a dilator and an air cannula over the fiber optic stylet and into the anatomical region of the person, and removing the dilator and fiber optic stylet leaving the air cannula in the anatomical region.

In another aspect, the anatomical region may include the tracheal lumen or where a patient's tracheal lumen bifurcates toward the main bronchus.

In another aspect, an artificial manual breathing unit or a ventilator may be connected to the air cannula to supply the patient with air.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed to a system and method for video assisted percutaneous needle cricothyrotomy and tracheostomy including an electronic display monitor, a percutaneous needle assembly including a syringe, a connection hub including a syringe port for removably attaching the syringe, a needle port for attaching a hollow needle, and a fiber optic port for receiving a fiber optic stylet that extends through the hollow needle. The fiber optic stylet includes one or more illuminators and a camera for capturing and transmitting anatomical images, where the anatomical images are displayed on the viewing screen of the electronic display monitor to properly identify and locate the trachea and trachea lumen to quickly ventilate patients with an air cannula.

Figure 1:
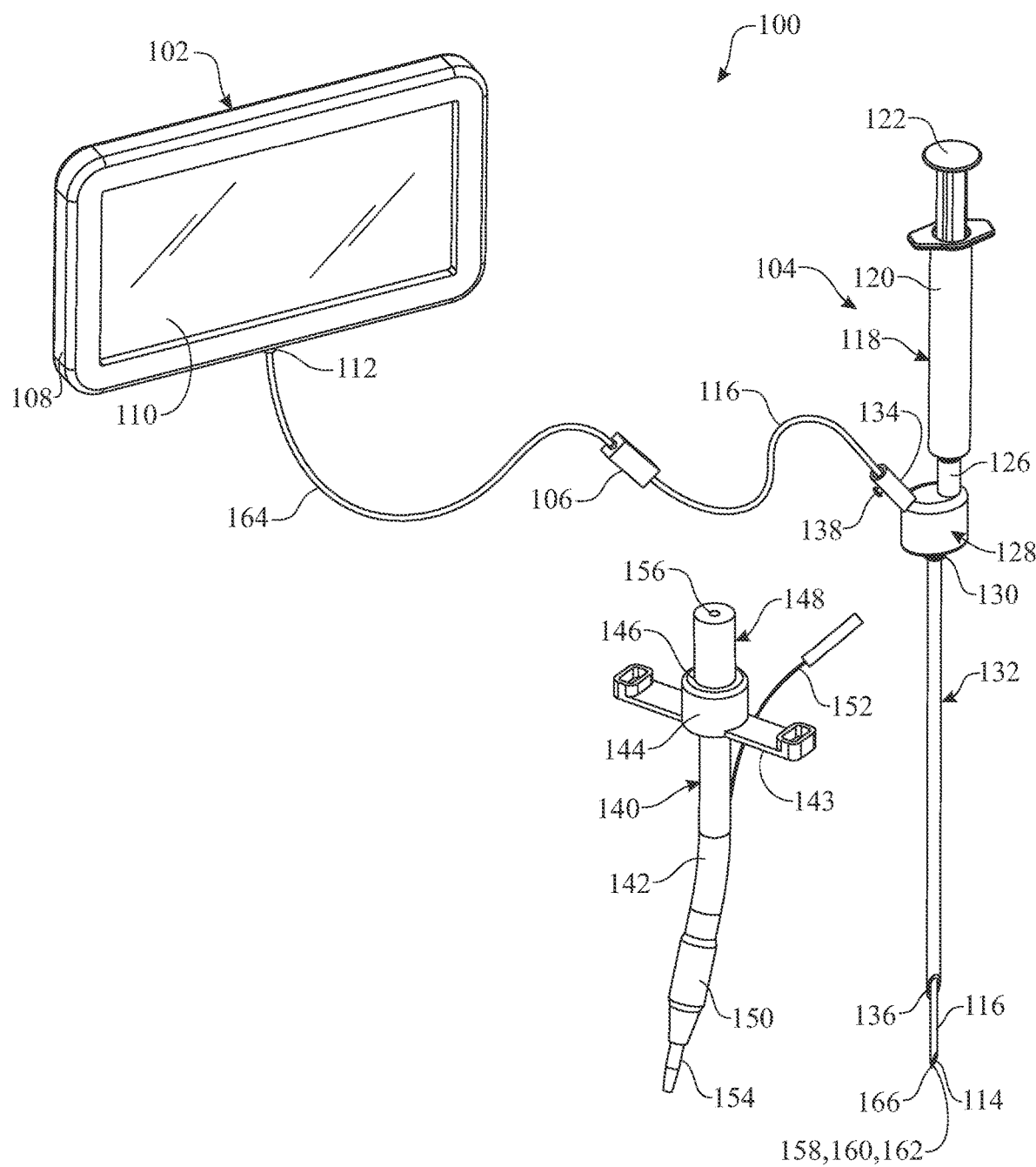
FIG. 1 presents a schematic view of a system and method for video assisted percutaneous needle cricothyrotomy and tracheostomy, showing an electronic display monitor, a percutaneous needle assembly including a syringe, a connection hub, a video communication system including an electronic display operative coupled to a fiber optic stylet via a communication module, and including a camera and one or more illuminators, and a dilator disposed within an air cannula, in accordance with an embodiment of the present invention.
Figure 2:
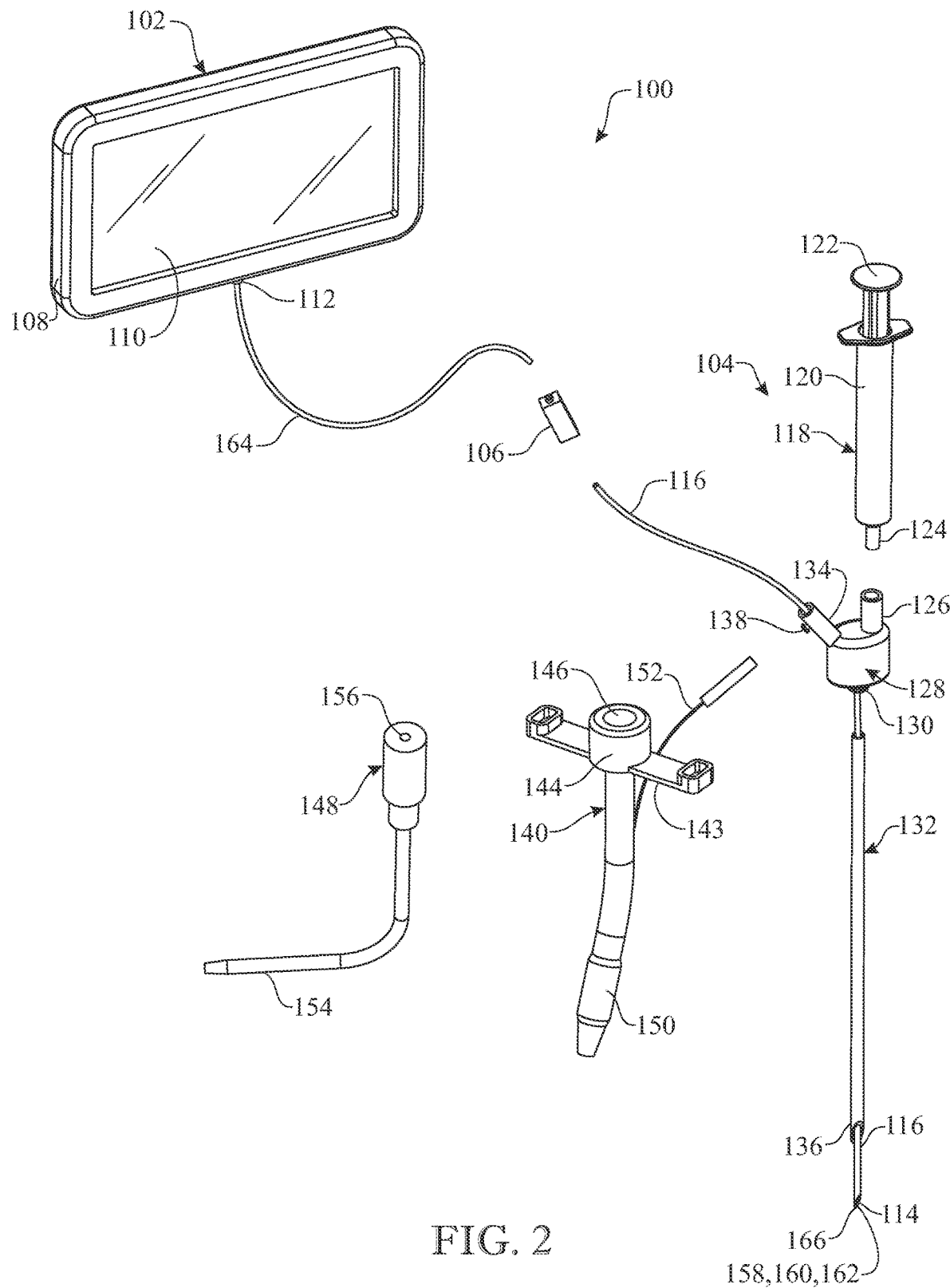
FIG. 2 presents an exploded view of the system and method for video assisted percutaneous needle cricothyrotomy and tracheostomy of FIG. 1, showing a syringe and hollow needle disconnected from the connection hub, the fiber optic stylet electrically disconnected from the electronic display monitor, via the communication module, and the dilator removed from the air cannula.

Referring now to the figures wherein like numerals are represented by like elements, throughout, there are shown in FIGS. 1 and 2, schematic views of a system and method for video assisted percutaneous needle cricothyrotomy and tracheostomy 100, showing an electronic display monitor 102, a percutaneous needle assembly 104, and a communication system 106 coupled to the electronic display monitor 102, in accordance with an embodiment of the present invention. The electronic or visual display monitor 102 generally comprises a housing 108 having a viewing screen 110, a communication port 112, and a series of electrical controls (not shown) operatively associated with electrical circuitry stored within the housing 108 for operating and controlling the electronic display monitor 102. Exemplary forms of the electrical controls may include, but are not limited to, an operative function to, turn the display monitor on/off, enlarge/reduce images, switch between still and video imaging modes, adjust brightness, contrast, sharpness, or color of images, and the option to save, delete, or edit images. The electrical circuitry includes the necessary electronic components needed to process video signals received and generated from a camera 114 provided, in one embodiment, at the distal end of a fiber optic stylet or stylet 116. As such, the electronic circuitry includes one or more processors, memory RAM, ROM, video network, network interface, and internal and/or external data storage. The electronic display monitor 102 may include high definition monitor interface (HDMI), universal series bus (USB) connections, optical or coaxial connections and capabilities, and is powered by AC and/or DC voltage power supply via, rechargeable batteries. In one embodiment, the electronic display monitor 102 may comprise any well-known medical video or image display monitor that is adapted for use with fiber optic imaging technology.

The percutaneous needle assembly 104 includes a syringe 118 including a housing 120 having a cavity for retaining a volume of air or liquid, and a plunger 122 that is operatively associated with the cavity for injecting a liquid into, or aspirating air from, a patient's trachea or tracheal lumen during a surgical airway procedure. The syringe 118 includes a syringe tip 124, (better illustrated in FIG. 2), having external or internal threads, or a lumen lock, that is adapted for attaching to a syringe port 126 provided on a connection hub 128. The connection hub 128 includes a needle port 130 for releasably connecting a hollow needle 132 thereto, and a stylet port 134 dimensionally adapted for receiving a fiber optic stylet 116. The stylet port 134 is in communication with the needle port 130 to permit the fiber optic stylet 116 to passes through the inner space of the connection hub 128, and slide within the hollow needle 132 when the hollow needle 132 is affixed to the needle port 130. As illustrated in FIG. 1, the distal end of the fiber optic stylet 116 is shown protruding slightly outwards from the beveled tip 136 of the hollow needle 132. The hollow needle 132 may include any predetermined length and gauge (such as 12, 14, 16, 18 gauge). In one non-limiting embodiment, the hollow needle 132 includes a beveled tip 136 that is designed to effectively and efficiently pierce a patient's skin causing little to no pain, damage or trauma to the patient. The syringe 118, and connection hub 128 are constructed from any well-known medical grade plastic material, and may include frictional properties that is provided on the outer surface of the body of the hub 128 to provide a firm, non-slip grip when holding the connection hub 128 in hand during a surgical airway procedure. Some examples of frictional properties may include ridges, dimples, grooves, or a rubber coating. In one non-limiting embodiment, the connection hub 128 may include an inner, dividing barrier (not shown) to help guide and direct the distal end of the fiber optic stylet 116 into the hollow needle 132 making it easy for physician's to quickly and correctly insert the fiber optic stylet 116 into the hollow needle 132 without the distal end of the fiber optic stylet 116 jamming or catching on inner surfaces of the connection hub 128.

As noted, connection hub 128 includes a release lock 138 that removably extends within the stylet port 134 to selectively engage the fiber optic stylet 116 to prevent the fiber optic stylet 116 from sliding freely within the hollow needle 132. The release lock 138 may comprise any of a rotating screw, a clamp, a spring-toggle member, a push in and out contactor, or other releasably, engagable member or mechanism. In use, physicians operate the release lock 138 for various reasons. For instance, the release lock 138 is used to prevent the fiber optic stylet 116 from moving when the distal end 166 of the fiber optic stylet 116 is coplanar with the beveled tip of the hollow needle 132 so that both ends can simultaneously enter a patient's anatomical regions or area such as through the skin or when entering the cricothyroid membrane, or to advance the distal end 166 of the fiber optic stylet 116 into a patient's trachea lumen during a surgical airway procedure. Upon determining that the distal end 166 of the fiber optic stylet 116 is correctly positioned within the patient's trachea lumen, physicians can operate the release lock 138 to remove the percutaneous needle assembly and retain the use of the fiber optic stylet 116 as a medical guide wire.

A cuff cricothyrotomy procedure generally employs the use of an air cannula generally denoted at 140. The air cannula 140 includes a cannula tube 142 having a predetermined length, and diameter, and is coupled to a hub 144 including an opening 146 for removably receiving a dilator 148. A cannula stopper 143 is integral with the hub 144 and designed to engage the outer surface of a patient's skin when the cannula tube 142 is inserted within the cricothyroid membrane to prevent the cannula tube 142 from sliding down further within the patient's tracheal lumen. An inflatable air cuff 150 is provided along the distal end of the cannula tube 142, and an air or liquid delivery connector 152 is in fluid communication with the air cuff 150 and releasably attachable to an air supply for delivering air to inflate the air cuff 150. The dilator 148 includes a dilator tube 154 having a predetermined length and diameter. The dilator tube 148 is inserted within the opening 146 of the hub 144 to extend through the cannula tube 142 and slightly outwards from the distal end of the cannula tube 142, as shown in FIG. 1. The dilator 148 includes an elongate aperture 156 that extends the length of the dilator tube 154 for receiving the fiber optic stylet 116 therein, as better illustrated in FIGS. 10 and 11. It is appreciated that the cannula tube 142 comprise a 20-degree angulation for properly aligning and placing the tube 142 within a patient's trachea 206 during a surgical airway procedure. As shown, dilator tube 154 is bendable in various angles, and includes a tapered distal tip for gradually expanding the incision opening to introduce the cannula tube 142.

Figure 3:
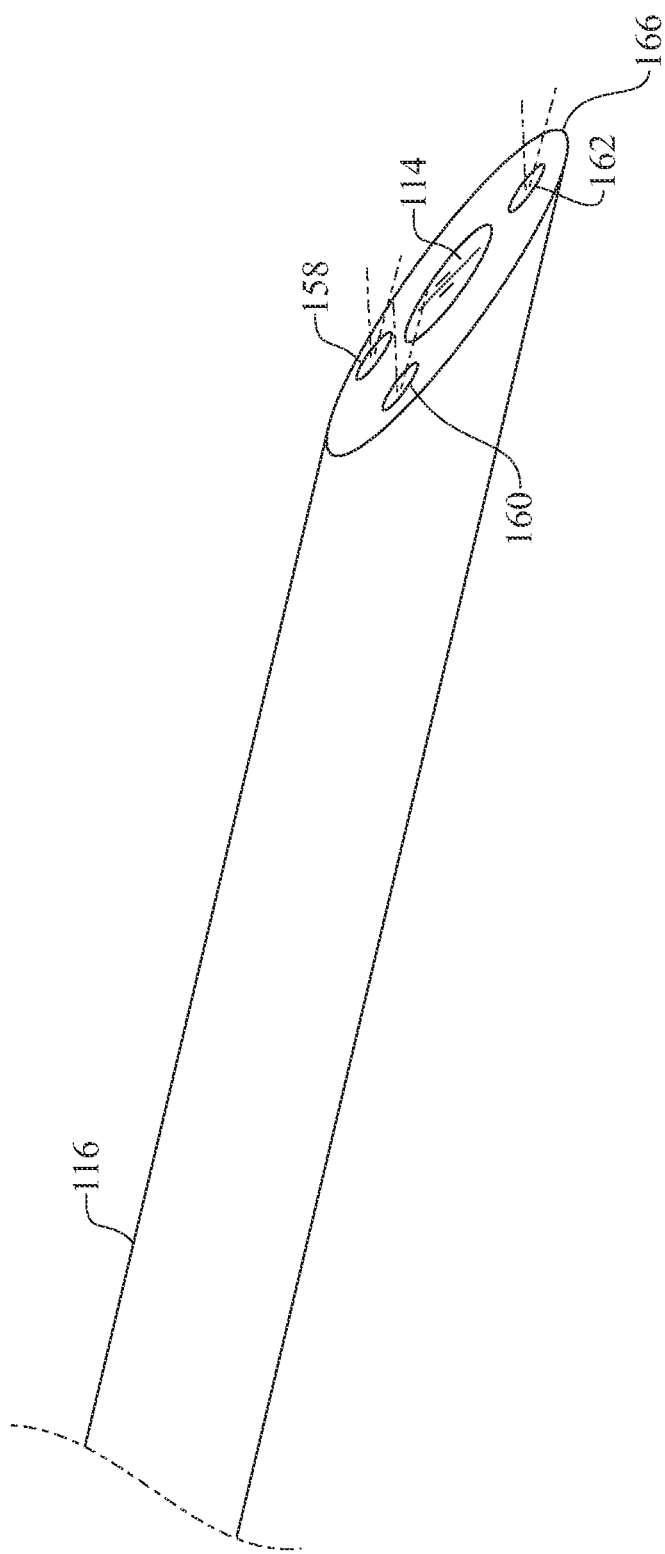
FIG. 3 presents a partial, side, perspective view of the fiber optic stylet, showing a distal end of the fiber optic stylet comprising a beveled shape, and including one or more illuminators, and a camera for capturing and transmitting anatomical images to the electronic display monitor.

As illustrated in FIG. 3, the fiber optic stylet 116 includes a miniature camera 114, and one or more illuminators 158, 160, 162, provided at the distal end of the fiber optic stylet 116. In one embodiment, illuminators 158, 160, 162 may include one or more light emitting diodes, or illuminating diodes, that are encased or disposed within the distal end of the fiber optic stylet 116. In one alternative embodiment, the illuminators 158, 160, 162 may include one or more light emitting diodes that are housed within the housing 108 of the electronic display monitor 102, and operatively coupled to the proximate end of the fiber optic stylet 116 so that when the one or more diodes are powered, light rays emanating from the powered diodes pass through the fiber optic stylet 116, or through designated regions of the fiber optic stylet 116, or through designated fiber optic cables encased within the fiber optic stylet 116, and outwards from the distal tip of the fiber optic stylet 116 to illuminate a patient's anatomical features when navigating with the distal end of the fiber optic stylet 116. The one or more light emitting diodes may comprise high intensity diodes, diodes the provide the same or different color light, and include top or side or top and side light emitting diodes. It is noted that one or more incandescent light bulbs may be used to replace the one or more light emitting diodes.

In one embodiment, the camera 114 is disposed and encased at the distal end of the fiber optic stylet 116, and configured to capture video or still images of the patient's anatomical features, and to transmit electrical signals associated with the captured images of the anatomical regions or features to the electronic display monitor 102 for processing and displaying images on the viewing screen 110. The camera 114 is in electrical or optical communication with the electronic display monitor 102, via the communication module 106. It is appreciated that in one alternative embodiment, the camera 114 may include a fiber optic camera in which one or more fibers are configured to transmit images from the distal end of the fiber optic stylet 116 which includes a powerful lens system, to a proximate end of the fiber optic stylet 116 which is operatively coupled to a camera enclosed in the electronic display monitor 102. For example, a camera may be enclosed within the housing 108 of the electronic display monitor 102, and operatively coupled to the fiber optic stylet 116 where the camera is designed to receive, and process images transmitted via, one or more image transferring fiber optic fibers, similar to functional attributes of visual endoscopes. The type of fiber optic stylet 116 and wiring topology selected depends on the application use. As such, the fiber optic stylet 116 may comprise a multi-mode or single-mode configuration where one or more fiber optic stylets are used to illuminate the front region of the fiber optic stylet 116, and one or more fiber optic stylets are used to transmit images. It is appreciated that camera 114 may comprise a charge coupled device (CCD), or a complementary metal oxide semiconductor CMOS image sensor It is contemplated that a variety of lens may be employed with illuminators 158, 160, 162, and/or with camera 114 to provide focus, magnification, to concentrate or collimate light rays emanating from the tip of the fiber optic stylet 116, to better focus video or still images captured by camera 114. Further, one or more translucent or colored filters may be employed to change the color of illuminated light, or to filter out light rays of particular electromagnetic radiation ranges. In relative comparison, the fiber optic stylet 116 may be similar in size to a medical guide wire commonly used to introduce cannulas within a patient, or is slightly larger. As such, the fiber optic stylet 116 may comprise any length, diameter or gauge for effective use in emergent cricothyrotomy or tracheostomy procedures. It is contemplated that the distal end of the fiber optic stylet 116 comprise a beveled end, a round end, an oval end, a rectangular end, a pointed end, or a cone-shaped end. In a preferred embodiment, the distal end of the fiber optic stylet 116 comprises a beveled end that is complimentary in shape to the distal beveled tip 136 of the hollow needle 132.

The system and method for video assisted percutaneous needle cricothyrotomy and tracheostomy 100 further includes a communication module 106 that is operatively connected to one end of the fiber optic stylet 116, and to a communication cable 164 for electrically or optically transmitting signals associated with captured images, and for powering illuminators 158, 160, and 162. In one embodiment, the communication module 106 comprises one or more transmitter/receiver, or transceiver modules compatible with, or available in digital visual interface (DVI), high-definition multimedia interface (HDMI), and serial digital interface (SDI). It will be understood that appropriate electrical or optical connectors, adaptors, and converters are implemented to coordinate the operative coupling of the stylet 116, and communication cable 164 together via, the communication module 106, and to the electronic display monitor 102. In applications where the communication cable 164 comprises a fiber optic cable, the image communication module 106 will comprise one or more transmitters/receivers or transceivers selected and used to operatively couple both the communication fiber optic cable 164 with the fiber optic stylet 116. However, in situations where the communication cable 164 comprises a coaxial cable, the communication module 106 will include a fiber optic-to-digital converter using appropriate connectors, and/or adaptors configured to couple the fiber optic stylet 116 to the communication coaxial cable 164. The communication module 106 may comprise any well-known devices, modules, adaptors, or converters engineered to provide the necessary coupling between fiber optic stylets, or between fiber optic stylets and coaxial cables, and to the electronic display monitor 102.

Figure 4:
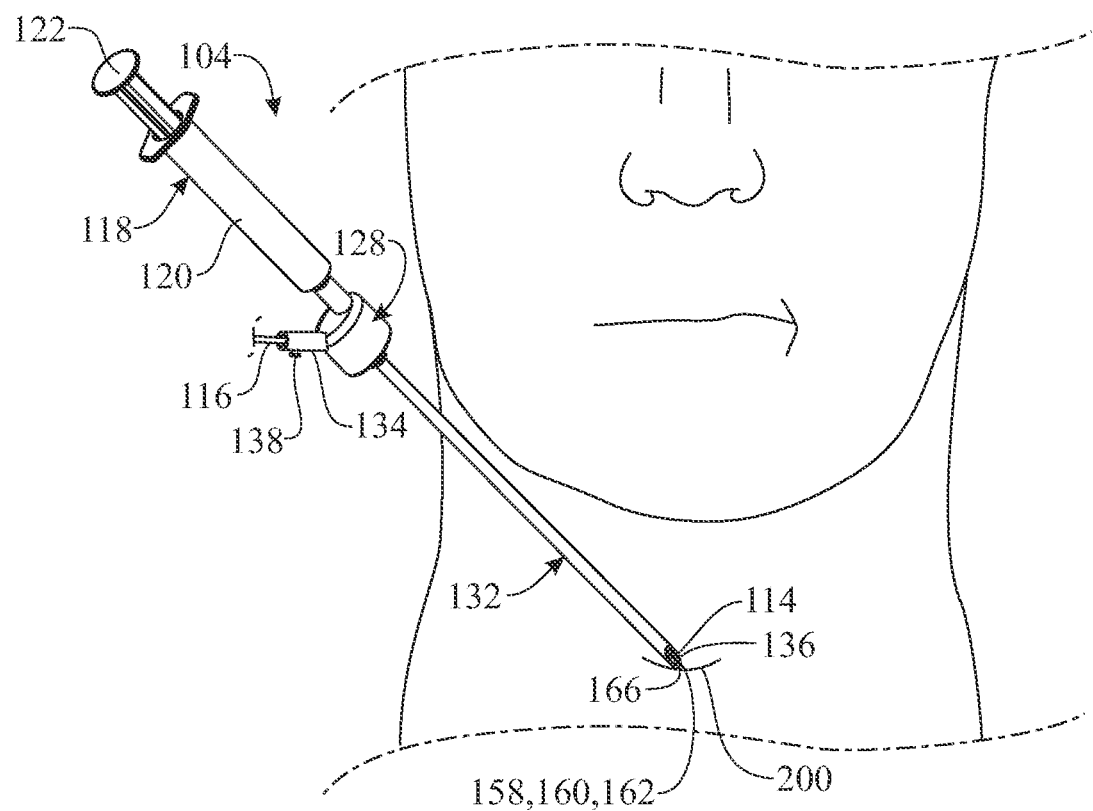
FIG. 4 presents a front, schematic view of the percutaneous needle assembly in use on a patient, showing a portion of the fiber optic stylet disposed within the hollow needle such that the distal end of the fiber optic stylet is coplanar with the distal tip of the hollow needle, where both the distal end of the fiber optic stylet and the distal tip of the hollow needle readily pierce and simultaneously enter, a patient's neck through the cricothyroid membrane.

Turning now to FIG. 4, there is shown an operative view of the percutaneous needle assembly 104 with the fiber optic stylet 116 inserted within the stylet port 134 and hollow needle 132 where the distal end of the fiber optic stylet 116 is aligned or coplanar with, the beveled tip 136 of the hollow needle 132. In practice, once the distal end of the fiber optic stylet 116 is aligned or coplanar with, the beveled tip 136 of the hollow needle 132, the physician can operate the release lock 138 to prevent the fiber optic stylet 116 from moving or sliding within the hollow needle 132 retaining the coplanar alignment of the beveled end of the fiber optic stylet 116 with the beveled tip 136 of the hollow needle 132.

Figure 5:
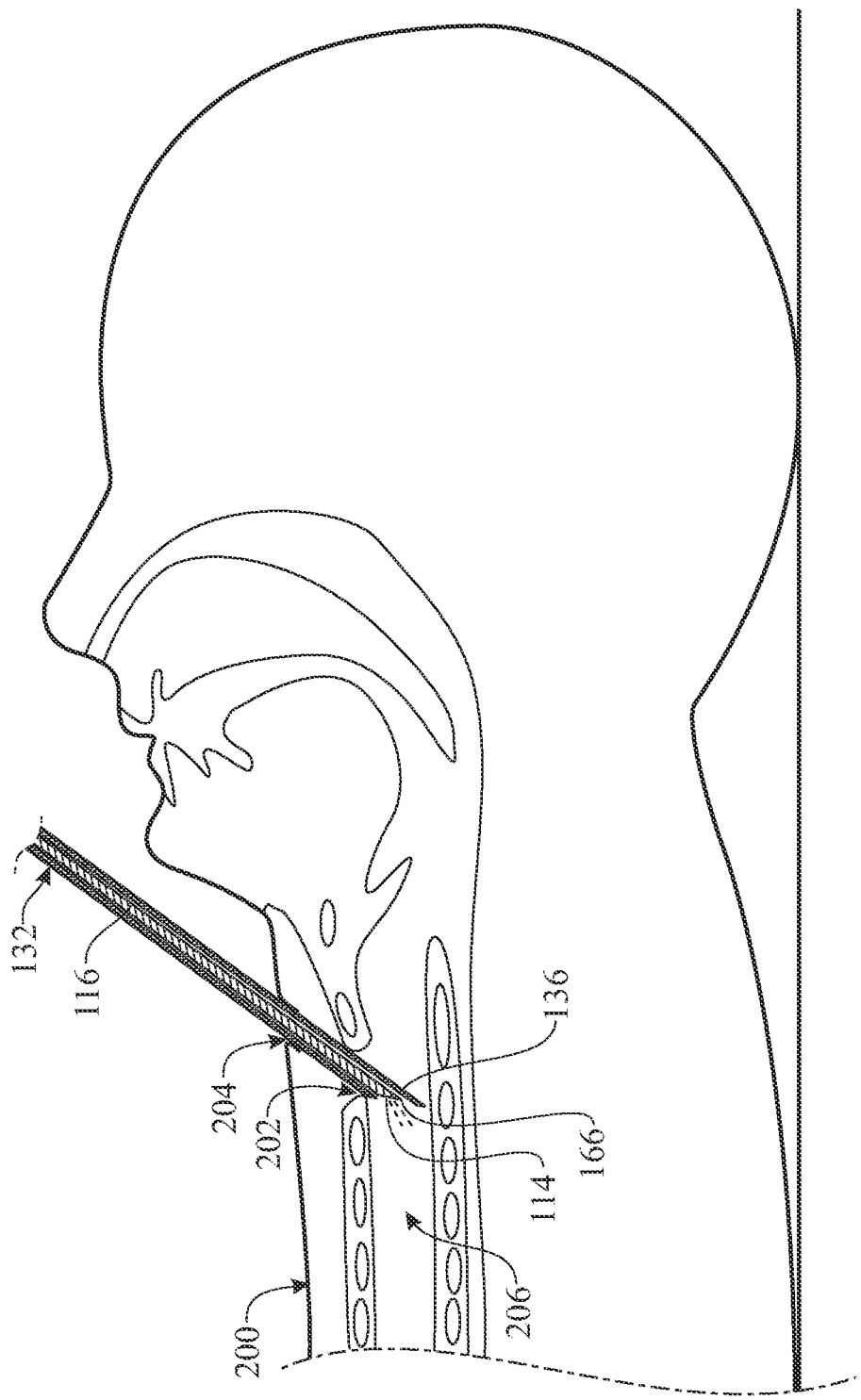
FIGS. 5 and 6 present partial, side views of a patient, showing a portion of the hollow needle and distal end of the fiber optic stylet extending through the patient's cricothyroid membrane, and the distal end of the fiber optic stylet directed into the trachea lumen with the one or more illuminators powered to illuminate the frontal region of the camera used for capturing and transmitting images of the patient's trachea lumen to the electronic display monitor.

In performing emergent needle percutaneous cricothyrotomy, the attending physician will typically palpate a patient's neck area 200 using fingers of one hand to touch and feel the patient's anatomical landmarks to determine the approximate location of the target puncture site identified as the cricothyroid membrane 202 which is located between the thyroid and cricoid cartilage, shown in FIG. 5. Palpation of the cricothyroid membrane 202 is a fairly simple procedure on a thin person, but is more challenging to identify and locate on patients who are obese, or have a thick neck as such anatomical landmarks are often distorted. In practice and preparation, a preparatory solution, such as betadine and local anesthesia, may be disposed on the neck area 200 of the patient. The physician then palpates the patient's neck 200 to determine the approximate location of the cricothyroid membrane 202 or surrounding tracheal ring.

Figure 7:
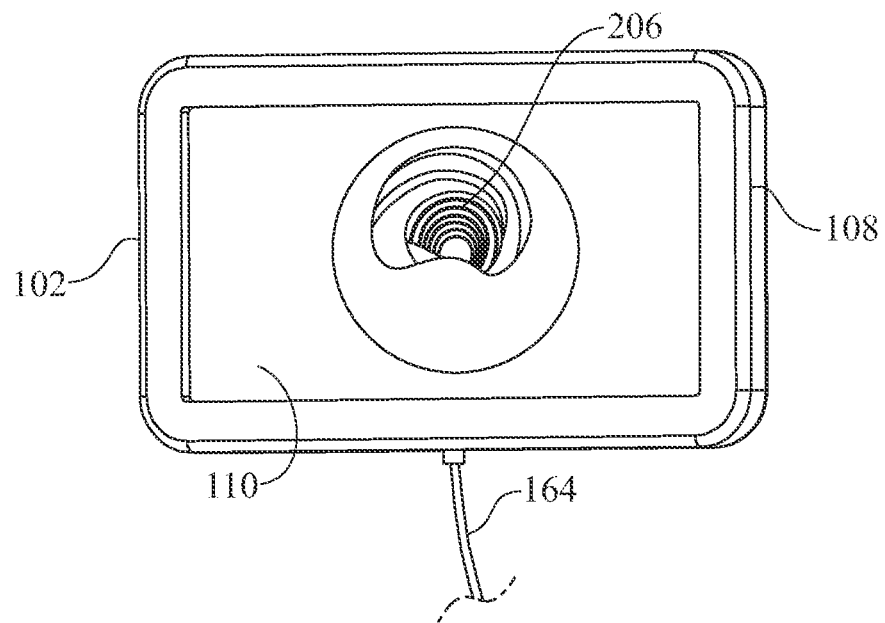
FIG. 7 presents a front, partial view of the electronic display monitor of FIG. 1, showing an image of a patient's trachea lumen captured by the camera of the fiber optic stylet in FIG. 6.
Figure 8:
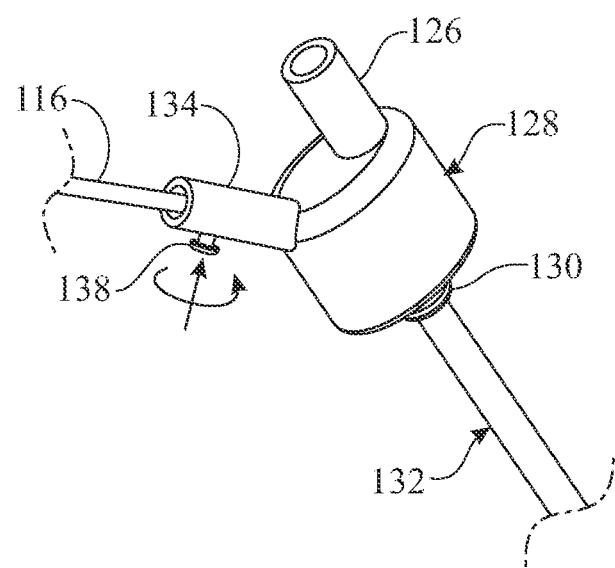
FIG. 8 presents a partial, side, perspective view of the percutaneous needle assembly of FIG. 1, showing a release lock provided on the stylet port of the connection hub for selectively preventing the fiber optic stylet from sliding freely within the stylet port and hollow needle.

In locating the target site, upon slight pressure of the hand, the beveled tip 136 of the hollow needle 132 is inserted through the patient's skin 204 as the attending physician provides a downward force gradually forcing the beveled tip 136 of the needle 132 through the fat and tissue of the patient's neck 200. The beveled tip 136 of the hollow needle 132 and beveled distal end of the fiber optic stylet 116 are simultaneously inserted through a patient's neck 200, and through the patient's cricothyroid membrane 202. As shown in FIG. 5, as the beveled tip 136 of the hollow needle 132, and the beveled distal end of the fiber optic stylet 116 enter the patient's cricothyroid membrane 202, illuminators 158, 160, 162 are powered to illuminate the frontal region of the camera 114 to provide visual guidance, and illuminate the region for the camera to capture video or still images of the patient's anatomical regions or parts that are transmitted to the electronic display monitor 102 for display on visual screen 110. The captured still or video images are processed in real time allowing the attending physician to quickly and effectively determine whether the distal end of the fiber optic stylet 116 is correctly located within the patient's tracheal lumen. As the physician navigates the distal tip of the hollow needle 132, and the distal end of the fiber optic stylet 116, the camera 114 continuously captures still or video images and transmits the captured still or video images or signals associated with the captured still or video images, to the electronic display monitor 102 for processing and displaying on the viewing screen 110 to provide viewable navigation to physicians for correctly and quickly locating the patient's trachea, as shown in FIG. 7. The beveled tip 136 of the hollow needle allows the attending physician to easily pierce a patient's skin with minimal pain, discomfort, and damage, and the fiber optic stylet 116 includes a camera 114 that allows physicians to quickly determine whether the end of the fiber optic stylet 116 is correctly located in the patient's tracheal lumen when preparing to insert an air cannula to ventilate the patient. Traditional or conventional systems and methods of locating a patient's trachea and tracheal lumen typically require repeated attempts to correctly insert the tip of a needle into the patient's trachea causing damage, more trauma, and discomfort to the patient, and further depleting the patient's odds of survival. The present system and method for video assisted emergency percutaneous needle cricothyrotomy and tracheostomy 100 allows physicians to quickly and accurately, visually locate a patient's trachea and tracheal lumen to perform emergency surgical airway procedures to adequately ventilate and oxygenate patients.

Figure 6:
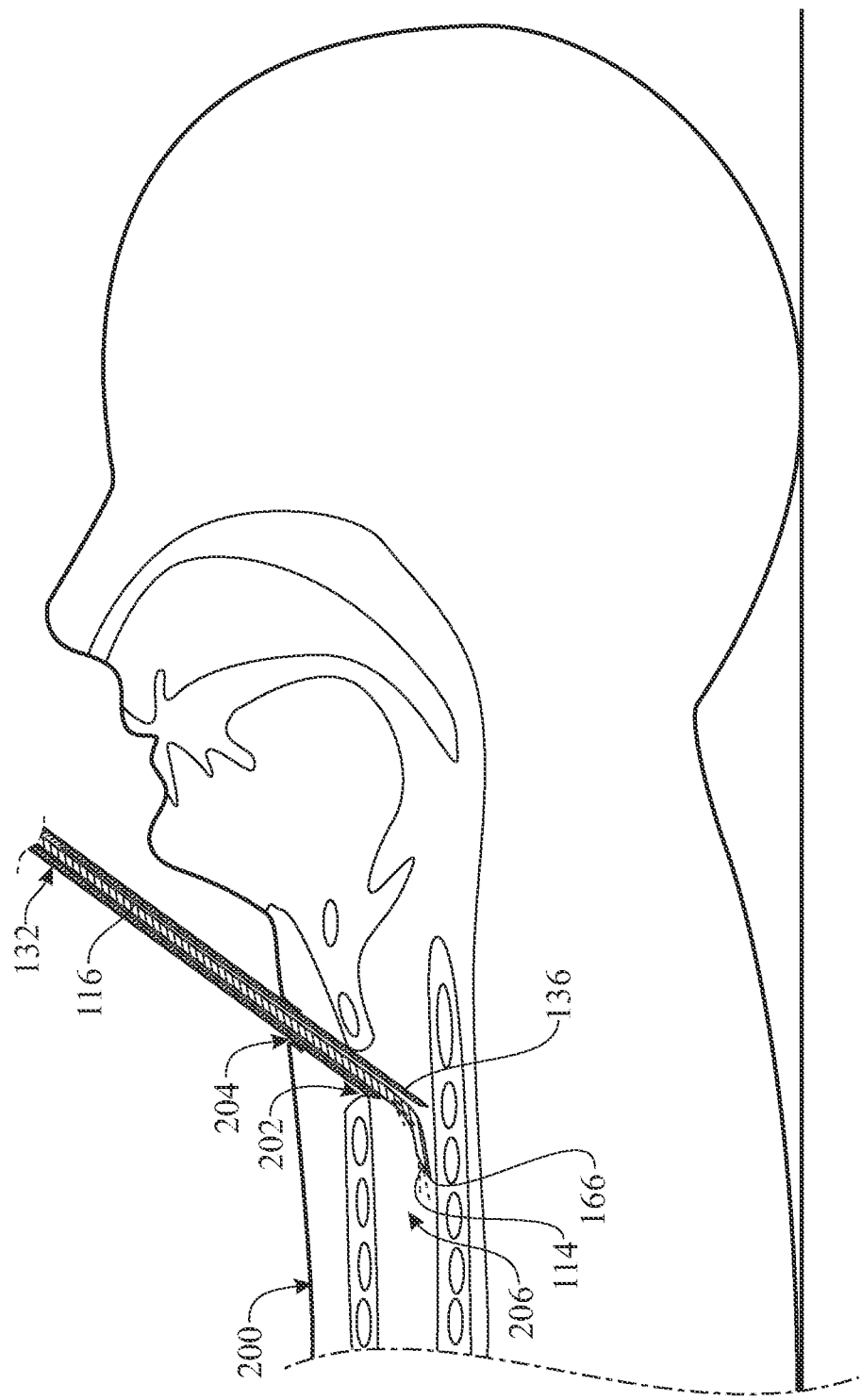

As illustrated in FIGS. 5 and 6, illuminators 158, 160, 162 effectively illuminate the frontal region of the camera 114 while the beveled tip 136 of the hollow needle 132 is negotiated within the patient's cricothyroid membrane 202. There may be instances in which the hollow needle 132 is redirected, or repositioned, to properly locate the patient's tracheal lumen 206. Once the physician has properly located the patient's trachea and tracheal lumen by viewing the viewing screen 110 on the electronic display monitor 102, as illustrated in FIG. 7, the physician may operate the release lock 138 to advance the distal end of the fiber optic stylet 116 within the trachea lumen. Physicians can visually determine, via, the viewing screen 110 of the electronic display monitor 102, whether the distal end of the fiber optic stylet 116 is correctly aligned within the patient's tracheal lumen 206.

Figure 9:
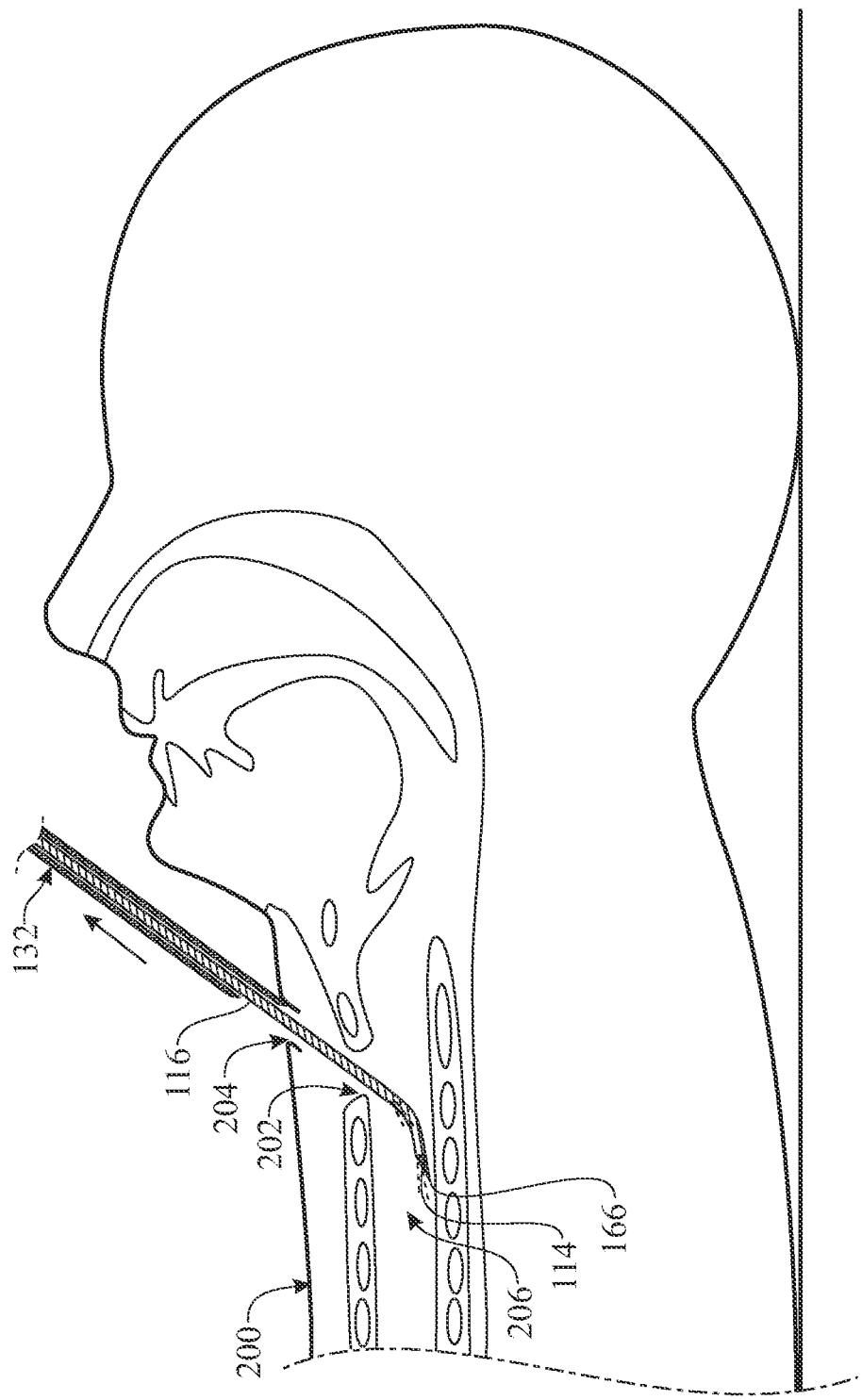
FIGS. 9, 10 and 11, present side, partial views of a patient, showing the fiber optic stylet used as a guide wire where the percutaneous needle assembly is removed, and dilator and air cannula are inserted over the guide wire and into the patient's trachea lumen to readily intubate and ventilate the patient.
Figure 10:
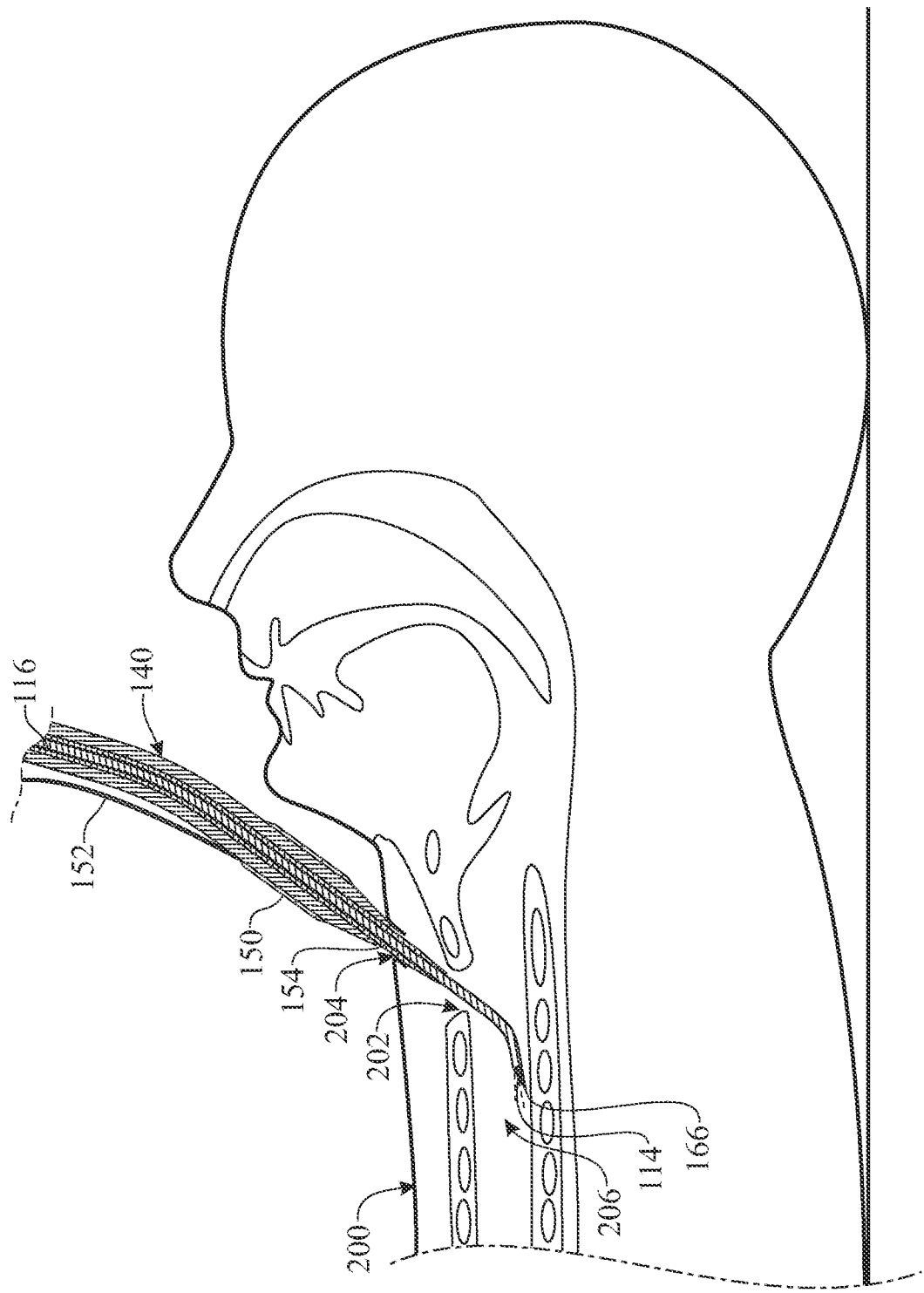
Figure 11:
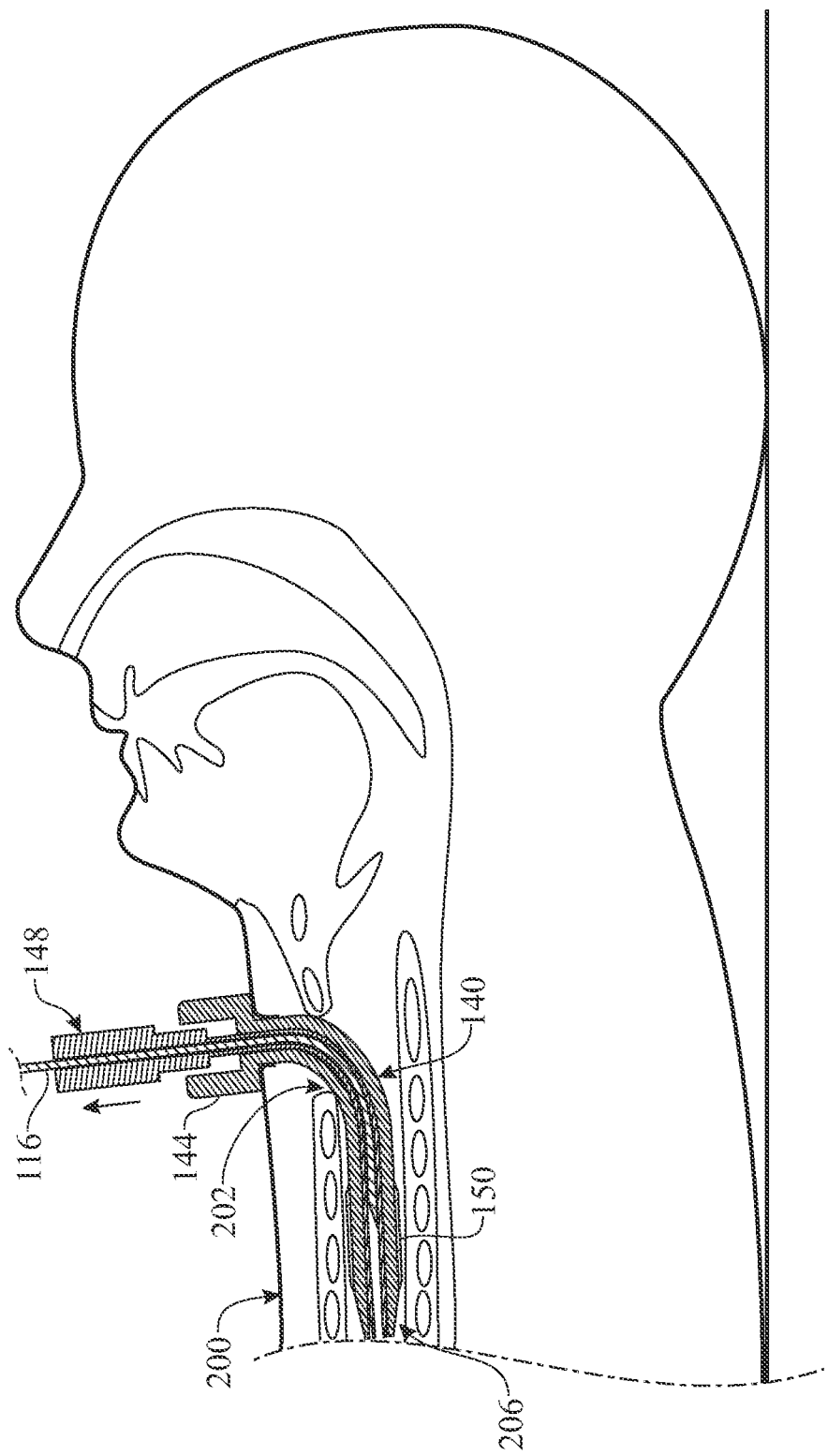

Turning to FIGS. 9, 10, and 11, there are presented partial, side views showing intubation of a patient with an air cannula 140, via an over the needle/stylet process in which the fiber optic stylet 116 used as a medical guide wire, in accordance with an embodiment of the present invention. Upon placing the distal end of the fiber optic stylet 116 correctly within the patient's trachea lumen 206, the physician proceeds to remove the percutaneous needle assembly 104 including the hollow needle 132 by sliding the hollow needle 132 upwards to expose the fiber optic stylet 116, as denoted by the directional arrow in FIG. 9. The release lock 138 is operated to remove engagement of the lock 138 with the fiber optic stylet 116 allowing the hollow needle 132 to slide freely upwards and along the fiber optic stylet 116. As shown in FIG. 2, the proximate end of the fiber optic stylet 116 is uncoupled from the communication module 106 to allow removing the connection hub 128 and hollow needle 132. While holding the fiber optic stylet 116 in place with one hand, the physician uses the fiber optic stylet 116 as a medical guide wire and inserts the dilator 148 and air cannula 142 combination over the fiber optic stylet 116, via inserting the proximate end of the fiber optic stylet 116 within the elongate aperture 156 of the dilator 148, and sliding the configured pair, i.e. the dilator 148 and attached cannula 140, downwards along the fiber optic stylet 116 such that both the dilator tube 154 and cannula tube 140 are displaced within the patient's tracheal lumen 206, as illustrated in FIG. 11. The extended tip of the dilator 148 extends outwards from the end of the air cannula tube 140, as shown in FIG. 1, and comprises a tapered shape designed to enter the incision or puncture site immediately prior to entry of the cannula tube 140. A small skin incision can be made with a scalpel along the fiber optic stylet 116 insertion site to facilitate entry of dilator 148, and cannula tube 140. As such, the tapered tip 154 of the dilator tube 148 gradually stretches the opening in the skin 204 to allow inserting of larger diameter air cannula tube 142. As such, the dilator 148 acts to gradually increase the opening of the skin 204 in preparation of inserting a larger diametrical body comprising the air cannula 140. In one non-limiting embodiment, the hollow needle 132 may include length markings to provide an estimate of the length of dilator 148 and/or cannula tube 140 needed for the surgical airway procedure.

Figure 12:
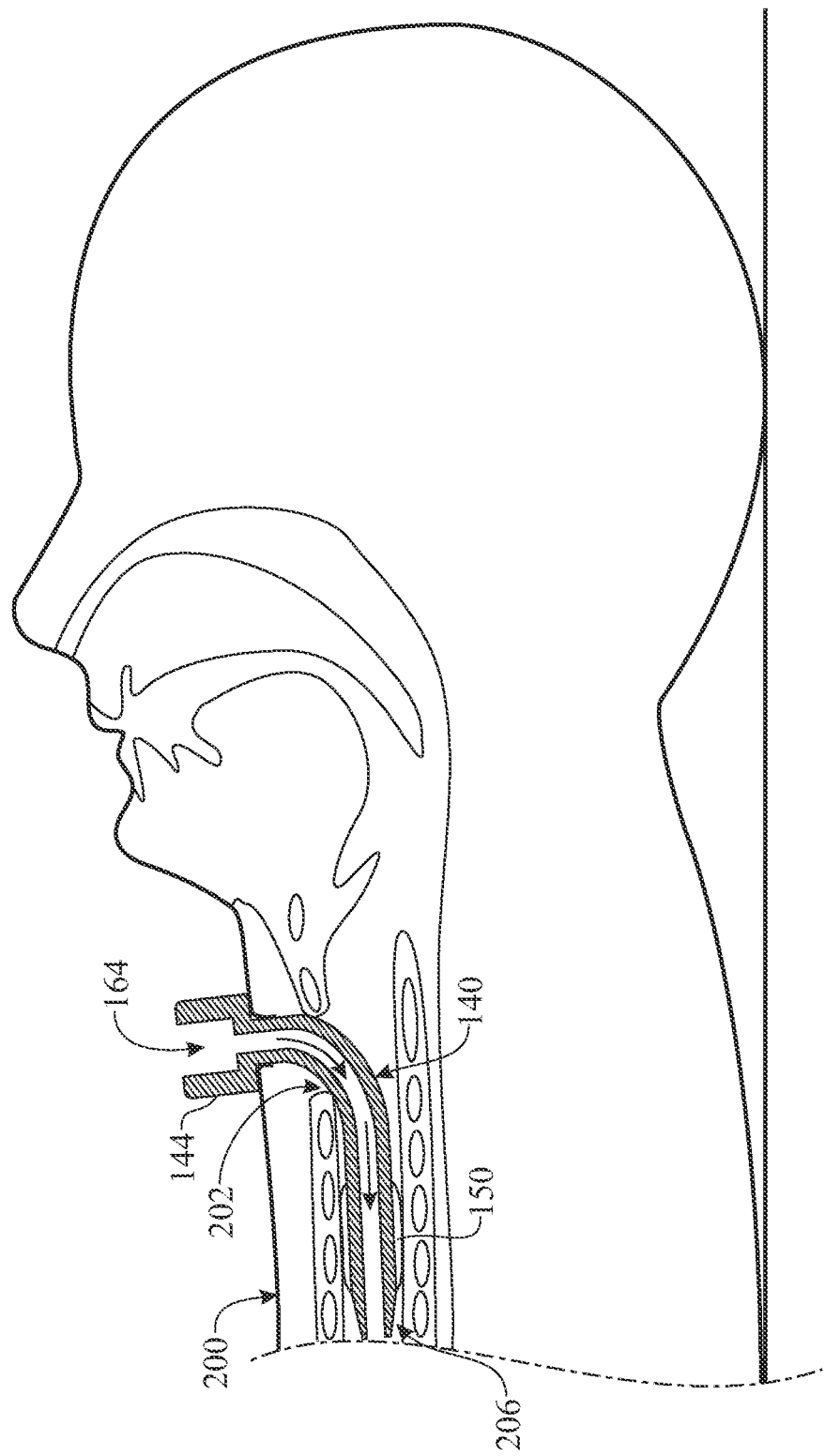
FIG. 12 presents a side, partial view of the patient of FIG. 11, showing the air cannula installed within the trachea lumen of the patient with the dilator completely removed, and the air cuff of the cannula readily inflatable to prevent the air cannula from moving within the trachea lumen.

As illustrated in FIGS. 11 and 12, upon inserting the air cannula tube 142 within the patient's tracheal lumen 206, the dilator 148 is subsequently removed, as denoted by the upwardly pointing directional arrow in FIG. 11. Air via, an air supply, is delivered via, 152 to inflate the cuff 150 of the cannula 140 in order to retain the air cannula 140 securely in place within the patient's tracheal lumen 206 to prevent the cannula 140 from dislodging, or popping out from the opening 204 provided in the patient's neck 200. As the air cannula 140 is intubated within the patient, air is delivered through the opening of the cannula tube 142 and into the patient's trachea 206, as indicated by arrow 164, in FIG. 12. A series of connectors or adaptors can implemented to removably attach an oxygen mask, or other ventilator equipment to the cannula 140 to forcibly oxygenate and ventilate the patient. The cannula stopper 143, as shown in FIG. 1, generally rests on the outer surface area of the patient's skin to prevent the cannula 140 or cannula tube 142 from sliding or advancing further within the patient's tracheal lumen.

The system and method for video assisted percutaneous needle cricothyrotomy and tracheostomy 100 includes a percutaneous needle assembly that includes a fiber optic stylet 116 which provides the functional benefit of illuminating the anatomical features of a person, capturing video or still images of such anatomical features using a camera 114 to help physicians efficiently and effectively locate the tracheal lumen of a patient during emergent surgical airway procedures, and operates as a medical guidewire that is used to properly intubate a patient using a dilator 148, and air cannula 142 to ventilate and oxygenate patients in repertory distress.

The system and method for video assisted percutaneous needle cricothyrotomy and tracheostomy 100 may include various features or improvements without departing from the scope of the invention. For example, the display monitor 102 may comprise a portable color monitor, a handle, a carrying case, and/or a vertical stand having a telescoping pole and support wheels to adjust the height of the display monitor 102, and easily transport the display monitor 102. In addition, the diameter of the hollow needle 132 may be selected to accommodate inserting of a fiber optic stylet 116 comprising a variety of different diameters. As such, the ports 126, 130, 134 of the connection hub 128 may be designed to accommodate differently sized needles 132, syringe tips 124, or fiber optic stylet or stylet 116. In one alternative embodiment, the illuminators 158, 160, 162, and camera 114 may be provided on the distal tip of the hollow needle 132 rather than on the distal end of the fiber optic stylet 116. In addition, the system and method 100 may be used by ENT for routine initial part routine tracheotomy procedure and by others like pulmonary critical care specialist for routine access to the trachea for per-cutaneous tracheotomies, which is different from routine tracheotomy. The fiber optic stylet 116 may be configured for use with laser interferometry, or interferometry to take micro-measurements of anatomical features, or used for video overlaying images.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:
1. A method of performing a cricothyroidotomy or a tracheostomy with a video-assisted system, including the steps of:
 providing a video-assisted system, comprising,
  a display monitor for displaying still or video images,
  a percutaneous needle assembly, comprising,
   a syringe port,
   a needle port,
   a stylet port in communication with the needle port,
   a hollow needle that includes a single lumen releasably attached to the needle port, the hollow needle including a beveled tip,
   a syringe including a cavity for holding a liquid or gas therein,
   a syringe tip in fluid communication with the cavity, and
   a plunger associated with the cavity and configured to extract or retract the liquid or gas through the syringe tip;
  a fiber optic stylet having a proximal end and a distal end that includes an image-capturing device and at least one illuminator;
  a communication module operatively coupled to the proximal end of the fiber optic stylet; and
  a communication transmitter for transmitting communication signals between the communication mod- ule, the image-capturing device, the at least one illuminator, and the display monitor;
locating an insertion site;
inserting the needle at the insertion site and positioning the needle at a desired anatomical region;
advancing the fiber optic stylet further into the anatomical region;
removing the needle from the first anatomical region leaving the fiber optic stylet in the anatomical region;
advancing a dilator and an air cannula over the fiber optic stylet and into the anatomical region; and
removing the dilator and fiber optic stylet leaving the air cannula in the anatomical region.

2. The method of claim 1, wherein the insertion site includes a person's cricothyroid or tracheal ring.

3. The method of claim 1, wherein the syringe tip is removably attached to the syringe port.

4. The method of claim 1, wherein the anatomical region includes a person's tracheal lumen.

5. The method of claim 1, wherein the anatomical region is visible on the display monitor.

6. The method of claim 1, wherein the anatomical region is a person's tracheal lumen bifurcation into the person's bronchus.

7. The method of claim 1, wherein an artificial manual breathing unit is attachable to the air cannula.

8. The method of claim 1, wherein a ventilator is attachable to the air cannula.

9. The method of claim 1, wherein the display monitor is transportable.

10. The method of claim 1, wherein the image-capturing device comprises a camera.

11. The method of claim 10, wherein the camera includes a charge-coupled device or a complementary metal oxide semiconductor image sensor.

12. The method of claim 1, wherein the at least one illuminator includes a plurality of illuminators each including a light-emitting diodes.

13. The method of claim 1, wherein the at least one illuminator includes one or more fiber optic cables coupled to an illumination source surrounding the image-capturing device.

14. The method of claim 1, wherein the distal end of the fiber optic stylet is removably insertable through the stylet port to extend through the needle port and slide within the hollow needle when the needle is affixed to the needle port.

15. The method of claim 1, wherein the images or video displayed on the display monitor is utilized to confirm the needle is in the desired anatomical region.

16. A method of performing a cricothyroidotomy or a tracheostomy with a video-assisted system, including the steps of:
providing a video-assisted system, comprising,
a display monitor for displaying still or video images,
a percutaneous needle assembly, comprising,
a syringe port,
a needle port,
a stylet port in communication with the needle port,
a hollow needle that includes a single lumen releasably attached to the needle port, the hollow needle including a beveled tip,
a syringe including a cavity for holding a liquid or gas therein,
a syringe tip in fluid communication with the cavity, and
a plunger associated with the cavity and configured to extract or retract the liquid or gas through the syringe tip;
a fiber optic stylet having a proximal end and a distal end that includes an image-capturing device and at least one illuminator;
a communication module operatively coupled to the proximal end of the fiber optic stylet; and
a communication cable having one end operatively coupled to the display monitor, and a second end operatively coupled to the communication module;
locating an insertion site;
inserting the needle at the insertion site and positioning the needle at a desired anatomical region;
advancing the fiber optic stylet further into the anatomical region;
decoupling the communication cable from the communication module;
removing the needle from the first anatomical region leaving the fiber optic stylet in the second anatomical region;
advancing a dilator and an air cannula over the fiber optic stylet and into the anatomical region of the person; and
removing the dilator and fiber optic stylet leaving the air cannula in the anatomical region.

17. The method of claim 16, wherein the image-capturing device and the at least one illuminator is operatively controlled by the display monitor via the communication module.

18. The method of claim 16, wherein the fiber optic stylet is insertable through the air cannula to confirm the air cannula is positioned correctly within the desired anatomical region.

19. The method of claim 1, wherein the anatomical region is a person's tracheal lumen bifurcation into the person's bronchus.

20. A method of performing a cricothyroidotomy or a tracheostomy with a video-assisted system, including the steps of:
providing a video-assisted system, comprising,
a display monitor for displaying still or video images,
a percutaneous needle assembly, comprising,
a syringe port,
a needle port,
a stylet port in communication with the needle port,
a hollow needle that includes a single lumen releasably attached to the needle port, the hollow needle including a beveled tip,
a syringe including a cavity for holding a liquid or gas therein,
a syringe tip in fluid communication with the cavity, and
a plunger associated with the cavity and configured to extract or retract the liquid or gas through the syringe tip;
a fiber optic stylet having a proximal end and a distal end that includes an image-capturing device and at least one illuminator;
a communication module operatively coupled to the proximal end of the fiber optic stylet; and
a communication cable having one end operatively coupled to the display monitor, and a second end operatively coupled to the communication module;
locating an insertion site;
inserting the needle at the insertion site and positioning the needle at a desired anatomical region;

advancing the fiber optic stylet further into the anatomical region;
decoupling the communication cable from the communication module;
removing the needle from the first anatomical region leaving the fiber optic stylet in the second anatomical region;
advancing a dilator and an air cannula over the fiber optic stylet and into the anatomical region of the person;
removing the dilator and fiber optic stylet leaving the air cannula in the anatomical region; and
connecting an artificial manual breathing unit or a ventilator to the air cannula.

\* \* \* \* \*